United States Patent

Mishra et al.

Patent Number: 5,486,533
Date of Patent: Jan. 23, 1996

[54] FUNGICIDAL SUBSTITUTED AZOLE DERIVATIVES

[75] Inventors: Anupama Mishra, Guelph, Canada; Robert A. Davis, Cheshire, Conn.

[73] Assignees: Uniroyal Chemical Company, Inc., Middlebury, Conn.; Uniroyal Chemical Ltd./Ltee, Elmira, Canada

[21] Appl. No.: 443,632

[22] Filed: May 18, 1995

Related U.S. Application Data

[62] Division of Ser. No. 263,096, Jun. 21, 1994, which is a continuation of Ser. No. 959,238, Oct. 9, 1992, abandoned.

[51] Int. Cl.$^6$ .................. A01N 43/653; C07D 249/08
[52] U.S. Cl. .................. 514/383; 548/267.2; 548/267.8; 548/268.6
[58] Field of Search .................. 514/383; 548/267.2, 548/267.8, 268.6

[56] References Cited

U.S. PATENT DOCUMENTS 4,559,077  12/1985  Regel et al. .................. 548/267.8

*Primary Examiner*—Patricia L. Morris
*Attorney, Agent, or Firm*—Daniel Reitenbach

[57] ABSTRACT

Compounds having the structural formula

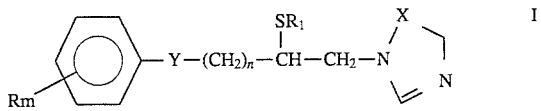

wherein:

R can be the same or different and is halogen, hydrogen, $C_1$–$C_8$ alkyl, $C_1$–$C_8$ haloalkyl, $C_3$–$C_6$ cycloalkyl, $C_7$–$C_9$ aralkyl, phenyl, nitro, $C_1$–$C_6$ alkoxy, $C_1$–$C_6$ alkylthio, $C_1$–$C_6$ alkylsulfinyl, $C_1$–$C_6$ alkylsulfonyl, $C_7$–$C_9$ aralkoxy, phenoxy, phenylthio, phenylsulfinyl, or phenylsulfonyl;

m is an integer from 0 to 5;

Y is $CH_2$, oxygen, or sulfur;

n is an integer from 0 to 5;

$R_1$ is $C_1$–$C_5$ alkyl, phenyl, $C_1$–$C_5$ alkyl substituted phenyl, or halogenated phenyl;

X is N or CH; or physiologically acceptable salts thereof are disclosed which have fungicidal activity. Fungicidal compositions comprising the compounds and a carrier are also disclosed, as are methods for controlling the growth of phytopathogenic fungi utilizing the compounds. Methods for the preparation of such compounds are also disclosed.

7 Claims, No Drawings

FUNGICIDAL SUBSTITUTED AZOLE DERIVATIVES

This is a division of application Ser. No. 08/263,096, filed Jun. 21, 1994, which is a continuation of application Ser. No. 07/959,238, filed Oct. 9, 1992, now abandoned.

BACKGROUND OF THE INVENTION

1. Field of the Invention

The present invention is directed to azole derivatives with alkylthio substituents useful as fungicides.

2. Description of Related Art

The control of phytopathogenic fungi is of great economic importance since fungal growth on plants or plant parts inhibits plant production and reduces the overall quality of the harvested crop.

To overcome or at least reduce the detrimental effects of fungi, plants have long been treated with fungicides. However, the enormous economic toll taken by identified fungi, as well as the development of new fungus strains resistant to known fungicides, establishes a continuing need to develop new and more effective fungicides which possess curative, preventative and systemic action to protect cultivated plants. These new fungicides must not only possess these protective properties but must not possess properties which have an adverse effect on the plants to be protected.

U.S. Pat. No. 4,078,071 is directed to derivatives of substituted N-alkyl imidazoles said to have antifungal, antibacterial, and antiprotozoal properties. U.S. Pat. 4,532,341 and 4,626,595 are directed to oxirane compounds said to be useful as plant growth regulants and fungicides. U.S. Pat. No. 4,626,594 is directed to a process for making the aforementioned oxiranes.

SUMMARY OF THE INVENTION

The present invention relates to substituted azole derivatives which provide effective control of many commonly encountered phytopathogenic fungi. The compounds have the structural formula

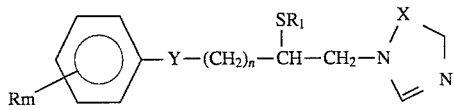

wherein:
R can be the same or different and is halogen, hydrogen, $C_1$–$C_8$ alkyl, $C_1$–$C_8$ haloalkyl, $C_3$–$C_6$ cycloalkyl, $C_7$–$C_9$ aralkyl, phenyl, nitro, $C_1$–$C_6$ alkoxy, $C_1$–$C_6$ alkylthio, $C_1$–$C_6$ alkylsulfinyl, $C_1$–$C_6$ alkylsulfonyl, $C_7$–$C_9$ aralkoxy, phenoxy, phenylthio, phenylsulfinyl, or phenylsulfonyl;
m is an integer from 0 to 5;
Y is $CH_2$, oxygen, or sulfur;
n is an integer from 0 to 5;
$R_1$ is $C_1$–$C_5$ alkyl, phenyl, $C_1$–$C_5$ alkyl substituted phenyl, or halogenated phenyl;
X is N or CH, with the proviso that when Y is $CH_2$ and $R_1$ is phenyl or substituted phenyl, then X is not CH; and physiologically acceptable salts thereof.

The present invention is also directed to fungicidal compositions comprising A) an active ingredient comprising a fungicidally effective amount of a compound having structure I above, and B) a suitable carrier therefor.

The present invention is also directed to a method of controlling fungi which comprises applying a fungicidally effective amount of a compound or composition of the present invention to the locus to be protected.

The present invention also includes a process for forming the compounds of structure I. In this process, an omega-haloalkyl substituted benzene undergoes a Grignard reaction to form an omega-alkenyl substituted benzene intermediate as pictured below:

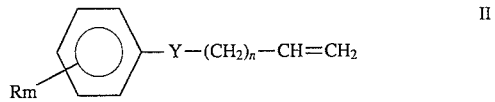

wherein Rm, Y, and n are as defined by the compound of structure I. This alkenyl is then reacted with $R_1SCl$ in the presence of calcium carbonate in dichloromethane to form the intermediate

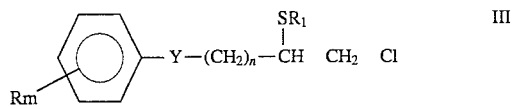

where $R_1$, R, m, Y, and x are defined as in structure I, and is reacted with triazole or imidazole to form the compounds of this invention.

DETAILED DESCRIPTION OF THE INVENTION

The compounds of the present invention have the structure I indicated above. Preferably, R is halogen or $C_2$–$C_4$ alkyl; m is 1 or 2; $R_1$ is $C_2$–$C_4$ alkyl; Y is $CH_2$, S, or O; and physiologically acceptable salts thereof.

More preferably, R is $C_2$–$C_4$ alkyl; m is 1; $R_1$ is $C_1$–$C_3$ alkyl; Y is $CH_2$; and X is CH; and physiologically acceptable salts thereof.

In a preferred embodiment, the substituent R is positioned para (in the 4-position) to the substituted benzene ring.

The present invention is also directed to an intermediate compound of the structural formula II or III as pictured above where R, $R_1$, m, Y, and n have the broadest meanings of the compound of structural formula I.

Preferably, the intermediate compound having the structural formula II or III is defined by R, $R_1$, m, Y, and n having the meanings of the preferred embodiment of the compound having structural formula I.

In addition to the compound having the structural formula I, the present invention encompasses physiologically acceptable salts thereof. These salts are obtainable by dissolving a compound having the structural formula I in a suitable inert solvent and adding an acid thereto. The reaction product is isolated and purified. For example, the product may be filtered and, if necessary, purified by washing with an inert organic solvent. The preferred acid utilized in the salt formation process is hydrochloric acid, resulting in the formation of the hydrochloride salt. Other suitable acids include nitric acid and sulfuric acid.

Yet another aspect of the present invention is a method for controlling phytopathogenic fungi. In this method a fungicidally effective amount of the compound having the structural formula I is applied to the locus to be protected from fungi.

In a preferred embodiment of the present method, the compound is applied to the foliage of the plants to be protected. This so-called "foliar treatment" is effectuated by applying the compound to the foliage at a concentration of between about 10 and about 500 milligrams of the compound per liter of inert liquid.

In another preferred embodiment of the present method, a fungicidally effective amount of the compound within the present invention is applied to the soil in which the plants to be protected from the fungi are grown. In this so-called "systemic treatment," the compound is applied to the soil in a concentration of between about 0.125 and about 10 kilograms of the compound per hectare (kg/ha) of soil. More preferably, the compound is applied at a concentration of between about 0.125 kg/ha to about 5 kg/ha.

Independent of which preferred embodiment of controlling fungi is utilized, either the foliar or systemic treatment, the application may be applied prior to or after infection by fungi. Furthermore, it should be appreciated that the exact dosage, applied systemically or to the foliage, is dictated by the fungus to be controlled and the particular plant to be protected.

In still another embodiment of the present method, the active ingredient is applied as a coating to the seeds of the plant to be protected. The fungicidal coating protects the soil from infection by the fungi and is also taken up by the plant systemically to protect the plant from fungal attack. In this so-called "seed coating method," an appropriate concentration of the active ingredient is in the range of between about 5 and about 75 grams per hundred kilograms of seed.

Another important aspect of the present invention resides in a new composition useful as a fungicide. The fungicidal composition of the present invention comprises A) an active ingredient comprising a fungicidally effective amount of a compound having the structural formula I above, and B) a suitable carrier.

Suitable carriers for the present compositions are wide ranging. The carrier may be a solid, for example, finely divided particulate solids, granules, pellets, wettable powders, soluble powders and the like. Among the solid carriers within the contemplation of the subject invention are such organic and inorganic materials as attapulgite clay, sand, vermiculite, corncob, activated carbon and mineral silicates. Among the mineral silicates preferred for use in the composition of the present invention are mica, talc, pyrophyllite, clays and the like.

A solid composition may be prepared from a solid carrier, such as one of those described immediately above. In that case, the active ingredient is impregnated onto the solid carrier. Alternatively, the active ingredient may be formulated into a wettable powder by grinding it into a fine powder and mixing it with the solid carrier to which a surface active dispersing agent has been added. The wettable powder is then dispersed in water and applied as a dispersion.

Indeed, the above described dispersion is representative of a composition which may also be classified as a liquid composition. In addition to liquid dispersions, the liquid composition may be in the form of a solution or an emulsion. In the case of a liquid solution, the active ingredient is dissolved in an aqueous or organic solvent. In most cases the solvent, which acts as the carrier, is organic. In addition to aromatic hydrocarbons, such as toluene and xylene, other preferred solvents include such organic compounds as acetone, methanol, isopropanol, t-butyl alcohol, cyclohexanone, dioxane, dimethylformamide, dimethyl sulfoxide, ethylene dichloride, diacetone alcohol and N-methylpyrrolidone.

A water emulsion, another preferred embodiment of a liquid composition within the contemplation of the present invention, is prepared from a solution, as described above, to which a surface active agent is added. Surface active agents suitable for use in forming an emulsion within the contemplation of this invention are known to those skilled in the art. *Mc Cutcheon's Detergents and Emulsifiers*, Allured Publishing Corp., Ridgewood, N.J. (1970); U.S. Pat. No. 2,514,916, at Columns 2 to 4; and U.S. Pat. No. 2,547,734, at Columns 3 and 4, provide detailed examples of such surface active agents suitable for this purpose. As indicated in these references, the surface active agent may be anionic, non-ionic or cationic.

In yet another embodiment, the carrier may be an aerosol. To prepare an aerosol, the active ingredient is dissolved in a first solvent. This first solvent is conventional in the sense that although it is volatile, it is not highly volatile. This solution is then admixed with a highly volatile solvent, a so-called liquid aerosol carrier. The aerosol carrier is liquid only under elevated pressure. At ambient temperature and pressure, the aerosol carrier is a gas. In a subembodiment of this preferred carrier, the aerosol carrier may itself be active. For example, the carrier may be an insecticide, a herbicide, a bacteriacide or the like.

The following examples are given to illustrate the present invention. Because these examples are given for illustrative purposes only, these examples should not be interpreted as limiting the invention to the scope of the examples recited hereinafter.

EXAMPLE 1

Preparation of
1-[3-[4-(1,1-dimethylethyl)phenyl]2-(methylthio) propyl-1H-1,2,4-triazole STEP 1
Preparation of 1-(1,1-dimethylethyl)-4-(2-propenyl) benzene (Intermediate Compound I-1)

To a Grignard reagent prepared from 12 g magnesium, 250 ml ether and 100 g 1-bromo-4-(1,1-dimethylethyl)benzene were added 50 g 3-chloro-1-propene dissolved in 150 ml ether. After the addition, the mixture was refluxed for one hour and kept stirring overnight at room temperature. The reaction mixture was then poured onto crushed ice and acidified with hydrochloric acid to dissolve any precipitated solid. The ether solution was separated, washed with water, and dried with anhydrous sodium sulfate, solvent removed and product distilled to provide 40 g of 1-(1,1-dimethylethyl)-4-(2-propenyl)benzene, listed in Table 1 as compound I-1. The product was characterized by a boiling point of 65°–66° C. at a pressure of 0.25 mm Hg.

STEP 2
Preparation of 4-(1,1,-dimethylethyl)-1-[3-chloro-2-(methylthio)propyl] -benzene (Intermediate compound I-26)

Methanesulfenyl chloride was prepared by dropwise addition of 20 g sulfuryl chloride to 20 g of dimethyl disulfide at a temperature of 0° to −5° C. This solution was then added to a mixture of 40 g of alkene prepared in the example above, 50 ml dichloromethane and 2 g calcium carbonate and kept between −65° to −70° C. The mixture was then allowed to come to room temperature and stirred for 10 hours. The solvent was removed and the product distilled to provide 45 g of 4-(1,1-dimethylethyl)-1-[3-chloro-2-(methylthio)propyl]benzene. This product was characterized by a boiling point of 140°–145° C. at a pressure of 0.1 mm Hg and is listed in Table 2 as compound I-26. Nuclear magnetic resonnace (nmr) spectra indicated the presence of small amounts of the isomeric addition product.

STEP 3
Preparation of 1-[3-[4-(1,1-dimethylethyl)phenyl]-2-(methylthio) propyl]1H-1,2,4-triazole (Compound No. 1)

A mixture of 3 g of the product of step 2 (Compound #I-26) 3 g triazole, 5 g anhydrous potassium carbonate in 30 ml of acetonitrile was refluxed for 7 hours, cooled, and the solvent removed. The residue was treated with water and ether and the ether layer was separated, washed twice with water, and dried. This compound is listed in Table 3 as compound 1. Removal of the ether gave two grams of an oil, which was characterized by nmr in Table 5.

EXAMPLE 2

Preparation of
1-[3-[4-(1,1-dimethylethyl)phenyl]-2-(methylthio) propyl]- 1H-imidazole (Compound, 35)

This compound was prepared following the procedure of Step 3 of Example 1 above using imidazole in place of triazole. It is listed in Table 4 as compound No. 35. The product was an oil characterized by nmr in Table 6.

EXAMPLE 3

Preparation of
1-[4-[4-(1,1-dimethylethyl)phenyl]-2(methylthio)butyl]-1H-1,2,4-triazole, hydrochloride (Compound No. 2)

STEP 1
Preparation of 1-(3-butenyl)-4-(1,1,-dimethylethyl)benzene (Compound I-2)

This compound was prepared following the procedure of step 1 of Example 1, using 1-bromomethyl-4-(1,1-dimethylethyl)benzene in place of 1-bromo-4-(1,1-dimethylethyl-)benzene, boiling point 78°–80° C. at 0.1 mm Hg.

Compound I-2 can also be prepared by reacting 1-bromomethyl-4-(1,1-dimethylethyl)benzene with the Grignard reagent prepared from from 3-bromo-1-propene.
STEP 2: Preparation of 1-[4-chloro-3-(methylthio)butyl]4-(1.1-dimethylethyl)benzene (Compound I -27)

This compound was prepared following the procedure of Example 1, Step 3, using the product of Example 3, Step 1 (1-(3-butenyl)-4-(1,1,-dimethylethyl)benzene: boiling point 145°–146° C. at 0.1 mm Hg. It is listed as compound I-27 in Table 2.
STEP 3
Preparation of 1-[4-[4-(1,1-dimethylethyl)phenyl]-2-(methylthio)butyl]-1H-1,2,4-triazole, hydrochloride. (Compound No. 2)

The triazole base was prepared by following the procedure of Example 1, Step 3 using the product of Example 2, Step 2 (1-[4-chloro-3-(methylthio)butyl]-4-(1,1-dimethylethyl) benzene) as the principle reagent. An oil thus obtained was dissolved in dry ether and dry hydrochloric gas was bubbled through it until a white solid precipitated. The product was filtered, washed twice with ether, and dried. Its melting point was found to be 125°–127° C. This compound is listed in Table 3 as compound 2.

EXAMPLE 4

Preparation of
1-[4-[4-(1,1-dimethylethyl)phenyl]-2-(methylthio) butyl]-1H-imidazole, hydrochloride (Compound No. 38)

This compound was prepared following the procedure of Example 3, Step 3 by using imidazole in place of trizaole. The melting point of the product was found to be 160°–165° C. as can be seen in Table 4, compound 38).

EXAMPLE 5

Preparation of
1-(1-dimethylethyl)-4-(4-penteyl)benzene
(Compound I-3)

A Grignard reagent was prepared from 10 g magnesium and 100 g 1-bromo-4-(1,1-dimethylethyl)benzene in 500 ml ether. Dry ethylene oxide was passed though this solution until the ether solution became a gel (about 20 g ethylene oxide). This gel was allowed to stand overnight and then decomposed with dilute hydrochloric acid. The ether layer was separated, washed with water, dried, and removed. Distillation gave 60 grams of 1-[(1-hydroxyethyl)-4-(1,1-dimethylethyl)]benzene, boiling point 100°–105° C. at 1 mm Hg.

Forty-five g of this compound was mixed with 60 g thionyl chloride in 50 ml toluene and refluxed for 5 hours. Removal of solvents and distillation yielded 30 g of 1-chloroethyl-4-(1,1-dimethylethyl) benzene, boiling point 95°–97° C. at 1 mm Hg.

This product 1-chloroethyl-4-(1,1-dimethylethyl) benzene) was converted to a Grignard reagent which was then coupled with 3-chloro-1-propene to yield 1-(1-dimethylethyl)-4-(4-pentenyl)benzene with a boiling point of 79°–80° C. at 0.2 mm Hg. The compound is listed in Table 1 as number I-3.

EXAMPLE 6

Preparation of
1-(1,1-dimethylethyl)-4-(2-propenyloxy)benzene
(Compound I-4)

A mixture of 45 g 4-(1,1-dimethylethyl)phenol, 30 g 3-chloro-1-propene, 50 g anhydrous potassium carbonate and 250 ml 2-butanone was refluxed for 15 hours, after which time the solvent was removed in a rotary evaporator. Water was added to dissolve the potassium salts and the product extracted twice with ether. The ether layer was dried, removed, and the product distilled. The 50 grams of 1-(1,1-dimethylethyl)-4-(2-propenyloxy)benzene was found to boil at 70°–75° C. at 0.2 mm Hg, listed in Table 1 as compound I-4)

EXAMPLE 7

Preparation of
1-(1,1-dimethylethyl)-4-(2-propenylthio)benzene.
(Compound I-5)

In 100 ml ethanol was dissolved 20 g 4-(1,1-dimethylethyl)benzenethiol and 8 g potassium hydroxide. To this solution was added 15 g 3-bromo-1-propne dropwise and the mixture was stirred at room temperature for twelve hours. This was filtered to remove insoluble solids, ethanol removed and the product distilled to yield 15 g 1-(1,1-dimethylethyl)-4-(2-propenylthio)benzene with a boiling point of 82°–185° C. at 0.1 mm Hg, listed in Table 1 as compound I-5.

EXAMPLE 8

Preparation of 1-(3-butenyl)-2-nitrobenzene and 1-(3-butenyl)-4-nitrobenzene (Compounds I-6, I-7)

A mixture of 100 g (3-butenyl)benzene and 500 ml acetic anhydride was cooled to 0° C. To this was added very slowly a solution of 60 ml concentrated nitric acid dissolved in a mixture of 60 ml acetic acid and acetic anhydride. After addition, the reaction mixture was stirred for two hours and then poured onto ice. This was saturated with salt and extracted with ether four times. The ethereal solution was washed twice with water, dried, and then the ether was removed. The distillate boiling between 90°–140° C., at 1 mm Hg, was collected and redistilled at 0.1 mm Hg.

Twenty grams were collected of 1-(3-butenyl)-2-nitrobenzene, Compound I-6, which boiled at 86°–91° C. at 0.1 mm Hg.

Fifteen grams of 1-(3-butenyl)-4-nitrobenzene, Compound I-7, were collected which boiled at 116°–118° C. at 0.1 mm Hg. Both of these are listed in Table 1.

EXAMPLE 9

Additional compounds within the scope of this invention were prepared using essentially the procedures outlined above. The structures and boiling points of intermediate compounds I-8 through I-25 are summarized in Table 1. The structures and boiling points of intermediate compounds I-26 through I-64 are summarized in Table 2.

EXAMPLE 10

Additional compounds within the scope of this invention were prepared using essentially the procedures outlined above. The structures and melting points of triazole compounds 1 through 34 are summarized in Table 3. The structures and melting points of imidazole compounds 35 through 66 are summarized in Table 4. NMR characterization of these compounds are presented in Tables 5 and 6, respectively.

Tables 1 through 6, containing lists of the intermediates and final products synthesized as well as NMR characterizations thereof, follow.

TABLE 1

$R_m$-C$_6$H$_4$-Y-(CH$_2$)$_n$-CH=CH$_2$

| Compound No. | Rm | Y | n | Physical constant b.p.(°C./mm) |
|---|---|---|---|---|
| I-1 | 4-C(CH$_3$)$_3$ | CH$_2$ | 0 | 65–66/.2 |
| I-2 | 4-C(CH$_3$)$_3$ | CH$_2$ | 1 | 78–80/.1 |
| I-3 | 4-C(CH$_3$)$_3$ | CH$_2$ | 2 | 79–80/.1 |
| I-4 | 4-C(CH$_3$)$_3$ | O | 1 | 70–75/.1 |
| I-5 | 4-C(CH$_3$)$_3$ | S | 1 | 82–85/.1 |
| I-6 | 2-NO$_2$ | CH$_2$ | 1 | 86–91/.1 |
| I-7 | 4-NO$_2$ | CH$_2$ | 1 | 116–118/.1 |
| I-8 | 4-Cl | CH$_2$ | 0 | 95–96/.3 |
| I-9 | 4-CH(CH$_3$)$_2$ | CH$_2$ | 1 | 65–66/.5 |
| I-10 | 4-Cl | CH$_2$ | 1 | 80–81/.2 |
| I-11 | 4-Cl | CH$_2$ | 2 | 73–75/.1 |
| I-12 | 4-Cl | CH$_2$ | 3 | 79–80/.2 |
| I-13 | H | CH$_2$ | 1 | 48–50/.1 |
| I-14 | 3-Cl | CH$_2$ | 1 | 38–40/.1 |
| I-15 | 4-OCH$_2$C$_6$H$_5$ | CH$_2$ | 1 | 140–145/.5 |
| I-16 | 4-OC$_5$H$_{11}$ | CH$_2$ | 1 | 106–108/.2 |
| I-17 | 3-OC$_5$H$_{11}$ | CH$_2$ | 1 | 100–102/.4 |
| I-18 | 2-C$_6$H$_5$ | CH$_2$ | 1 | 94–96/.5 |
| I-19 | 2-CH$_3$ | CH$_2$ | 1 | 55–60/.1 |
| I-20 | 2-CH$_2$OCH$_4$H$_9$ | CH$_2$ | 1 | 90–95/.2 |
| I-21 | 2-Cl | CH$_2$ | 1 | 80–81/.2 |
| I-22 | 3-OCH$_2$C$_6$H$_5$ | CH$_2$ | 1 | 150–152/.8 |
| I-23 | 2-OCH$_3$ | CH$_2$ | 1 | 58–60/.2 |
| I-24 | 2-OCH(CH$_3$)$_2$ | CH$_2$ | 1 | 64–66/.5 |
| I-25 | 3-CH$_2$OCH$_3$ | CH$_2$ | 1 | 68–70/.1 |

TABLE 2

$R_m$-C$_6$H$_4$-Y-(CH$_2$)$_n$CHCH$_2$Cl with SR$_1$ substituent

| Compound No. | Rm | Y | n | R | (b.p. °C./mm) |
|---|---|---|---|---|---|
| I-26 | 4-C(CH$_3$)$_3$ | CH$_2$ | 0 | CH$_3$ | 140–145/.1 |
| I-27 | 4-C(CH$_3$)$_3$ | CH$_2$ | 1 | CH$_3$ | 145–146/.1 |
| I-28 | 4-C(CH$_3$)$_3$ | CH$_2$ | 0 | CH(CH$_3$)$_2$ | 140–145/.1 |
| I-29 | 4-Cl | CH$_2$ | 0 | CH$_3$ | 145–150/.5 |
| I-30 | 4-C(CH$_3$)$_3$ | CH$_2$ | 0 | C$_4$H$_9$ | 135–140/.5 |
| I-31 | 4-C(CH$_3$)$_3$ | CH$_2$ | 1 | CH$_2$CH$_3$ | 150–155/.1 |
| I-32 | 4-C(CH$_3$)$_3$ | CH$_2$ | 1 | C$_4$H$_9$ | 160–165/.1 |
| I-33 | 4-C(CH$_3$)$_3$ | CH$_2$ | 1 | CH(CH$_3$)$_2$ | 145–146/.1 |
| I-34 | 4-C(CH$_3$)$_2$ | CH$_2$ | 1 | CH$_3$ | 132–135/.1 |
| I-35 | 4-C(CH$_3$)$_2$ | CH$_2$ | 1 | CH(CH$_3$)$_2$ | 145–146/.1 |
| I-36 | 4-Cl | CH$_2$ | 1 | CH$_3$ | 135–140/.1 |
| I-37 | 4-Cl | CH$_2$ | 1 | CH(CH$_3$)$_2$ | 140–142/.1 |
| I-38 | 4-C(CH$_3$)$_3$ | O | 1 | CH$_3$ | 150–153/.2 |
| I-39 | 4-C(CH$_3$)$_3$ | O | 1 | CH(CH$_3$)$_2$ | 150–155/.1 |
| I-40 | 4-C(CH$_3$)$_3$ | CH$_2$ | 1 | Ph | 180–185/.1 |
| I-41 | 4-C(CH$_3$)$_3$ | S | 1 | CH$_3$ | 160–163/.1 |
| I-42 | 4-C(CH$_3$)$_3$ | S | 1 | CH(CH$_3$)$_2$ | 165–170/.1 |
| I-43 | 4-C(CH$_3$)$_3$ | CH$_2$ | 2 | CH$_3$ | 175–180/.3 |
| I-44 | 4-C(CH$_3$)$_3$ | CH$_2$ | 2 | CH(CH$_3$)$_2$ | 170–175/.1 |
| I-45 | 4-Cl | CH$_2$ | 2 | CH$_3$ | 140–145/.2 |
| I-46 | 4-Cl | CH$_2$ | 2 | CH(CH$_3$)$_2$ | 160–165/.2 |
| I-47 | 4-Cl | CH$_2$ | 3 | CH(CH$_3$)$_2$ | 165–170/.1 |
| I-48 | 4-Cl | CH$_2$ | 3 | CH$_3$ | 160–162/.1 |
| I-49 | H | CH$_2$ | 1 | CH$_3$ | 120–125/.1 |
| I-50 | 4-NO$_2$ | CH$_2$ | 1 | CH$_3$ | 190–195/.5 |
| I-51 | 3-Cl | CH$_2$ | 1 | CH$_3$ | 140–142/.1 |
| I-52 | 4-OC$_5$H$_{11}$ | CH$_2$ | 1 | CH$_3$ | 205–210/.2 |
| I-53 | 3-OC$_5$H$_{11}$ | CH$_2$ | 1 | CH$_3$ | 168–170/.3 |
| I-54 | 2-C$_6$H$_5$ | CH$_2$ | 1 | CH$_3$ | 200–210/.5 |
| I-55 | 2-CH$_3$ | CH$_2$ | 1 | CH$_3$ | 130–135/.1 |
| I-56 | 2-CH$_2$OC$_4$H$_9$ | CH$_2$ | 1 | CH$_3$ | 166–168/.2 |
| I-57 | 2-NO$_2$ | CH$_2$ | 1 | CH$_3$ | 165–168/.2 |
| I-58 | 2-Cl | CH$_2$ | 1 | CH$_3$ | 140–145/.3 |
| I-59 | 3-OCH$_2$—C$_6$H$_5$ | CH$_2$ | 1 | CH$_3$ | 195–210/.1 |
| I-60 | 4-OCH$_2$—C$_6$H$_5$ | CH$_2$ | 1 | CH$_3$ | 180–182/.5 |
| I-61 | 2-OCH$_3$ | CH$_2$ | 1 | CH$_3$ | 135–127/.3 |
| I-62 | 2-OCH(CH$_3$)$_2$ | CH$_2$ | 1 | CH$_3$ | 160–165/.1 |
| I-63 | 4-Cl | CH$_2$ | 1 | C(CH$_3$)$_3$ | 190–195/.1 |
| I-64 | 3-CH$_2$OCH$_3$ | CH$_2$ | 1 | CH$_3$ | 160–165/.1 |

TABLE 3

![structure: phenyl(Rm)-Y-(CH2)n-CH(SR1)-CH2-N(triazole)]

| Compound No. | Rm | Y | n | R1 | Salt | m.p. °C. |
|---|---|---|---|---|---|---|
| 1 | 4-C(CH₃)₃ | CH₂ | 0 | CH₃ | — | oil |
| 2 | 4-C(CH₃)₃ | CH₂ | 1 | CH₃ | HCl | 125–127 |
| 3 | 4-Cl | CH₂ | 0 | CH₃ | HCl | 115–117 |
| 4 | 4-C(CH₃)₃ | CH₂ | 0 | C₄H₉ | — | oil |
| 5 | 4-C(CH₃)₃ | CH₂ | 0 | CH(CH₃)₂ | — | oil |
| 6 | 4-C(CH₃)₃ | CH₂ | 1 | CH₂CH₃ | — | oil |
| 7 | 4-CH(CH₃)₂ | CH₂ | 1 | CH₃ | HCl | 185–192 |
| 8 | 4-CH(CH₃)₂ | CH₂ | 1 | CH₃ | — | oil |
| 9 | 4-CH(CH₃)₂ | CH₂ | 1 | CH(CH₃)₂ | HCl | 100–102 |
| 10 | 4-CH(CH₃)₂ | CH₂ | 1 | CH(CH₃)₂ | — | oil |
| 11 | 4-Cl | CH₂ | 1 | CH₃ | — | oil |
| 12 | 4-Cl | CH₂ | 1 | CH(CH₃)₂ | — | oil |
| 13 | 4-C(CH₃)₃ | O | 1 | CH₃ | HCl | 125–130 |
| 14 | 4-C(CH₃)₃ | O | 1 | CH(CH₃)₂ | HCl | 110–112 |
| 15 | 4-C(CH₃)₃ | CH₂ | 1 | CH(CH₃)₂ | — | oil |
| 16 | 4-C(CH₃)₃ | CH₂ | 1 | CH(CH₃)₂ | HCl | 60–65 |
| 17 | 4-C(CH₃)₃ | CH₂ | 1 | C₄H₉ | — | oil |
| 18 | 4-C(CH₃)₃ | CH₂ | 1 | C₄H₉ | HCl | oil |
| 19 | 4-C(CH₃)₃ | CH₂ | 1 | C₆H₅ | HCl | 115–120 |
| 20 | 4-C(CH₃)₃ | S | 1 | CH₃ | — | oil |
| 21 | 4-C(CH₃)₃ | S | 2 | CH(CH₃)₂ | — | oil |
| 22 | 4-C(CH₃)₃ | CH₂ | 2 | CH₃ | — | oil |
| 23 | 4-Cl | CH₂ | 2 | CH(CH₃)₂ | — | oil |
| 24 | 4-C(CH₃)₃ | CH₂ | 2 | CH(CH₃)₂ | — | oil |
| 25 | 4-Cl | CH₂ | 3 | CH₃ | — | oil |
| 26 | 4-Cl | CH₂ | 2 | CH₃ | — | oil |
| 27 | H | CH₂ | 1 | CH₃ | — | oil |
| 28 | 4-NO₂ | CH₂ | 1 | CH₃ | — | oil |
| 29 | 3-Cl | CH₂ | 1 | CH₃ | — | oil |
| 30 | 4-OCH₂—C₆H₅ | CH₂ | 1 | CH₃ | — | oil |
| 31 | 4-OC₅H₁₁ | CH₂ | 1 | CH₃ | — | oil |
| 32 | 3-OC₅H₁₁ | CH₂ | 1 | CH₃ | — | oil |
| 33 | 4-Cl | CH₂ | 1 | C(CH₃)₃ | — | oil |
| 34 | 3-CH₂OCH₃ | CH₂ | 1 | CH₃ | — | oil |

TABLE 4

![structure: phenyl(Rm)-Y-(CH2)n-CH(SR1)-CH2-N(imidazole)]

| Compound No. | Rm | Y | n | R1 | Salt | m.p. °C. |
|---|---|---|---|---|---|---|
| 35 | 4-C(CH₃)₃ | CH₂ | 0 | CH₃ | — | oil |
| 36 | 4-C(CH₃)₃ | CH₂ | 1 | CH₃ | — | oil |
| 37 | 4-C(CH₃)₃ | CH₂ | 1 | C₄H₉ | — | oil |
| 38 | 4-C(CH₃)₃ | CH₂ | 1 | CH₃ | HCl | 160–165 |
| 39 | 4-CH(CH₃)₂ | CH₂ | 1 | CH(CH₃)₂ | — | oil |
| 40 | 4-Cl | CH₂ | 1 | CH(CH₃)₂ | — | oil |
| 41 | 4-C(CH₃)₃ | O | 1 | CH(CH₃)₂ | — | oil |
| 42 | 4-C(CH₃)₃ | CH₂ | 1 | C₄H₉ | HCl | 55–60 |
| 43 | 4-CH(CH₃)₂ | CH₂ | 1 | CH(CH₃)₂ | HCl | 135–140 |
| 44 | 4-Cl | CH₂ | 1 | CH(CH₃)₂ | HCl | 100–102 |
| 45 | 4-Cl | CH₂ | 2 | CH₃ | — | oil |
| 46 | 4-Cl | CH₂ | 2 | CH(CH₃)₂ | — | oil |
| 47 | 4-C(CH₃)₃ | CH₂ | 2 | CH(CH₃)₂ | HCl | oil |
| 48 | 4-Cl | CH₂ | 3 | CH₃ | HCl | oil |
| 49 | 4-C(CH₃)₃ | CH₂ | 2 | CH₃ | — | oil |
| 50 | H | CH₂ | 1 | CH₃ | — | oil |
| 51 | 4-Cl | CH₂ | 1 | C(CH₃)₃ | — | oil |
| 52 | 2-CH₃ | CH₂ | 1 | CH₃ | — | oil |
| 53 | 4-CH(CH₃)₂ | CH₂ | 1 | CH₃ | — | oil |
| 54 | 2-NO₂ | CH₂ | 1 | CH₃ | — | oil |
| 55 | 4-NO₂ | CH₂ | 1 | CH₃ | — | oil |
| 56 | 2-Cl | CH₂ | 1 | CH₃ | — | oil |
| 57 | 3-Cl | CH₂ | 1 | CH₃ | — | oil |
| 58 | 4-Cl | CH₂ | 1 | CH₃ | — | oil |
| 59 | 3-OCH₂—C₆H₅ | CH₂ | 1 | CH₃ | — | oil |
| 60 | 4-OCH₂—C₆H₅ | CH₂ | 1 | CH₃ | — | oil |
| 61 | 2-C₆H₅ | CH₂ | 1 | CH₃ | — | oil |
| 62 | 2-OCH₃ | CH₂ | 1 | CH₃ | — | oil |
| 63 | 4-OC₄H₁₁ | CH₂ | 1 | CH₃ | — | oil |
| 64 | 2-OCH(CH₃)₂ | CH₂ | 1 | CH₃ | — | oil |
| 65 | 3-OC₅H₁₁ | CH₂ | 1 | CH₃ | — | oil |
| 66 | 3-CH₂OCH₃ | CH₂ | 1 | CH₃ | — | oil |

TABLE 5

NMR Characteristics of Triazole Compounds Listed in Table 3

| Cmpd. No. | |
|---|---|
| 1 | S(9)1.2; S(3)1.9; m(3)3.0; d(2)4.3; m(4)7.2; S(1)7.9; S(1)8.4 |
| 4 | m(3)0.9; S(9)1.3; m(4)1.5; m(2)2.2; m(3)2.9; d(2)4.3; m(4)7.3; S(1)7.9; S(1)8.1 |
| 5 | d(6)1.1; S(9)1.3; m(4)2.9; d(2)4.2; m(4)7.3; S(1)7.9; S(1)8.1 |
| 6 | t(3)1.2; S(9)1.3; m(5)2.9; d(2)4.2; m(4)7.3; S(1)7.9; S(1)8.1 |
| 8 | d(6)1.3; m(2)1.9; S(3)2.0; m(4)2.8; d(2)4.2; m(4)7.2; S(2)8.2 |
| 10 | d(2)1.3; m(2)1.9; m(5)3.0; d(2)4.4; m(4)7.2; S(1)8.0; S(1)8.2 |
| 11 | m(2)1.9; S(3)2.1; m(3)2.8; d(2)4.3; m(4)7.1; S(1)7.9; S(1)8.2 |
| 12 | d(6)1.2; m(2)1.8; m(4)2.9; d(2)4.4; m(4)7.2; S(1)8.1; S(1)8.6 |
| 15 | d(6)1.2; S(9)1.4; m(2)1.9; m(4)2.8; d(2)4.3; m(4)7.2; S(1)7.0; S(1)8.2 |
| 17 | m(3)0.9; S(9)1.4; m(6)1.8; m(2)2.3; m(3)2.9; d(2)4.2; m(4)7.2; S(1)7.9; S(1)8.2 |
| 20 | S(9)1.3; S(3)2.0; m(3)3.1; d(2)4.4; m(4)7.3; S(1)7.9; S(1)8.1 |
| 21 | d(6)1.2; S(9)1.3; m(4)3.1; d(2)4.4; m(4)7.3; S(1)7.9; S(1)8.1 |
| 22 | S(9)1.3; m(4)1.5; S(3)1.9; m(3)2.8; d(2)4.3; m(4)7.3; S(1)7.9; S(1)8.1 |
| 23 | d(6)1.2; m(4)1.5; m(4)2.8; d(2)4.2; m(4)7.2; S(1)7.9; S(1)8.1 |
| 24 | d(6)1.2; S(9)1.3; m(4)1.5; m(4)2.7; d(2)4.2; m(4)7.2; S(1)7.9; S(1)8.1 |
| 25 | m(6)1.6; S(3)1.9; m(3)2.7; d(2)4.3; m(4)7.2; S(1)7.9; S(1)8.1 |
| 26 | m(4)1.5; S(3)1.8; m(3)2.8; d(2)4.2; m(4)7.1; S(1)7.9; S(1)8.1 |
| 27 | m(2)1.8; S(3)1.9; m(3)2.9; d(2)4.3; m(5)7.2; S(1)7.9; S(1)8.1 |
| 28 | m(2)1.8; S(3)1.9; m(3)2.9; d(2)4.2; m(6)7.3 and 8.2 |
| 29 | m(2)1.8; S(3)1.9; m(2)2.8; m(1)3.2; d(2)4.2; m(4)7.1; S(1)7.9; S(1)8.1 |
| 30 | m(2)1.8; S(3)1.9; m(3)2.8; d(2)4.2; S(2)5.0; m(9)7.2; S(1)7.9; S(1)8.1 |
| 31 | m(3)1.0; m(6)1.5; m(2)1.8; S(3)1.9; m(3)2.8; t(2)4.0; d(2)4.2; m(4)7.0; S(1)8.1 |
| 32 | m(3)1.0; m(6)1.5; m(2)1.8; S(3)1.9; m(3)2.8; t(2)4.0; d(2)4.2; m(4)7.0; S(1)7.9; S(1)8.1 |
| 33 | S(9)1.2; m(2)1.8; m(3)2.8; d(2)4.4; m(4)7.2; S(1)8.2 |
| 34 | m(2)1.8; S(3)1.9; m(3)2.8; S(3)3.3; d(2)4.0; S(2)4.4; m(6)7.1 |

TABLE 5-continued

NMR Characteristics of Triazole Compounds Listed in Table 3

Cmpd. No.

Remarks
(i) Solvent - $CDCL_3$
(ii) S = Singlet, d = doublet, t = triplet, m = multiplet
(iii) The number in parenthesis represents the number of protons
(iv) The number following the parenthesis is the chemical shift in & values.

TABLE 6

NMR Characteristics of Imidazole Derivatives Listed in Table 4

| Cmpd. No. | |
|---|---|
| 35 | S(9)1.3; S(3)2.0; m(2)3.0; m(1)3.5; d(2)4.0; m(7)7.2 |
| 36 | S(9)1.3; m(2)1.6; S(3)1.9; m(3)2.8; d(2)4.0; m(7)7.2 |
| 37 | m(3)0.9; S(9)1.3; m(6)1.5; m(2)2.3; m(3)2.8; d(2)4.0; m(7)7.2 |
| 39 | m(12)1.2; m(2)1.6; m(5)2.8; d(2)4.0; m(7)7.1 |
| 40 | d(6)1.2; m(2)1.7; m(4)2.8; d(2)4.0; m(7)7.2 |
| 41 | d(6)1.2; S(9)1.3; m(2)2.8; m(2)4.0; m(2)4.3; m(7)7.1 |
| 45 | m(4)1.6; S(3)1.9; t(2)2.5; m(1)2.8; d(2)4.1; m(7)7.2 |
| 46 | d(6)1.3; m(4)1.5; t(2)2.5; m(2)2.9; d(2)4.0; m(7)7.3 |
| 47 | d(6)1.2; S(9)1.3; m(4)1.6; t(2)2.5; m(2)2.8; d(2)4.0; m(7)7.2 |
| 48 | m(6)1.6; S(3)2.0; m(2)2.6; m(1)3.1; d(2)4.4; m(4)7.3; S(1)7.8; S(1)8.0; S(1)9.4 |
| 49 | S(9)1.3; m(4)1.6; S(3)1.8; m(3)2.8; d(2)4.0; m(7)7.3 |
| 50 | m(2)1.8; S(3)1.9; m(3)2.8; d(2)4.0; m(8)7.1 |
| 51 | S(9)1.2; m(2)1.8; m(3)2.7; m(2)4.0; m(7)7.0 |
| 52 | m(2)1.8; S(3)1.9; S(3)2.2; m(3)2.8; d(2)4.0; m(7)7.1 |
| 53 | d(6)1.3; m(2)1.9; S(3)2.0; m(4)2.8; d(2)4.0; m(7)7.1 |
| 54 | m(2)1.8; S(3)1.9; m(3)2.9; d(2)4.1; m(7)7.5 |
| 55 | m(2)1.8; S(3)1.9; m(3)2.9; d(2)4.3; m(7)7.3 and 8.1 |
| 56 | m(2)1.8; S(3)1.9; m(3)2.9; d(2)4.1; m(7)7.2 |
| 57 | m(2)1.8; S(3)1.9; m(3)2.8; d(2)4.1; m(7)7.2 |
| 58 | m(2)1.8; S(3)1.9; m(3)2.8; d(2)4.1; m(7)7.2 |
| 59 | m(2)1.8; S(3)1.9; m(3)2.8; d(2)4.0; S(2)5.0; m(12)7.0 and 7.3 |
| 60 | m(2)1.8; S(3)1.9; m(3)2.8; d(2)4.0; S(2)5.0; m(12)7.0 and 7.3 |
| 61 | m(2)1.8; S(3)1.9; m(3)2.8; d(2)4.0; m(12)7.3 |
| 62 | m(2)1.8; S(3)1.9; m(3)2.8; S(3)2.8; d(2)4.0; m(7)7.0 |
| 63 | m(3)1.0; m(6)1.5; m(2)1.8; S(3)1.9; m(3)2.8; m(4)4.0; m(7)7.0 |
| 64 | d(6)1.3; m(2)1.8; S(3)1.9; m(3)2.8; d(2)4.0; m(1)4.5; m(7)7.0 |
| 65 | m(3)0.9; m(6)1.4; m(2)1.8; S(3)1.9; m(3)2.8; m(4)4.0; m(7)7.3 |
| 66 | m(2)1.8; S(3)1.9; m(3)2.8; S(3)3.3; d(2)4.2; S(2)4.4; m(5)7.2; S(1)7.9; S(1)8.2 |

Remarks
(i) Solvent - $CDCL_3$
(ii) S = Singlet, d = doublet, t = triplet, m = multiplet
(iii) The number in parenthesis represents the number of protons
(iv) The number following the parenthesis is the chemical shift in & values.

EXAMPLE 11

Preparation of Fungicidal Compositions

Compound Nos. 1 to 66, summarized in Tables 3 and 4 above, were each dissolved in acetone or other suitable solvent (0.3 g. of each of the compounds in 10 ml. of acetone or other suitable solvent). One or two drops of an emulsifying agent, Triton [trademark] X-100, and water were added to the solution to form an emulsion. The amount of water added was a function of the desired concentration of the emulsion composition, reported in milligrams per liter (mg/l).

EXAMPLE 12

Control of Powdery Mildew Fungus by Systemic Root Uptake

Compositions of Compound Nos. 1 to 66, formed in accordance with the procedure of Example 11, were tested to evaluate their effectiveness in preventing or controlling powdery mildew disease of barley caused by the fungus, *Erysiphe graminis* and powdery mildew disease of cucumber caused by the fungus,*Erysiphe cichoracearum*. This prevention or control capability was tested by utilizing the compounds of the present invention to control these diseases by systemic root uptake.

In accordance with this aim, pots (4×4×3.5 inches) containing 10 plants of barley (Variety "Herta") or 5 plants of cucumber (Variety "Marketmore 76") were grown to an age of six days and ten days, respectively. Upon reaching these ages, emulsion compositions (45 ml.) of Compounds 1 to 66, formed in accordance with the procedure of Example 11, were added to each pot. That is, 45 ml. of an emulsion composition of each of the compounds tabulated in Tables 3 and 4 were separately added to pots containing 10 barley or 5 cucumber plants of the type enumerated above. The 45 ml. of each of the emulsion compositions were added to each of the pots and saturated the soil in each pot without significant loss through drainage into the saucers below the pots. Each of the compositions contained the compounds of the present invention in a concentration of 250 milligrams of the compound per liter of water (mg/l). A number of pots containing the same barley and cucumber plants were left untreated as controls.

The barley and cucumber plants in all the pots, including those treated and those untreated, were inoculated with powdery mildew fungus 24 hours after emulsion composition treatment with the compounds of the present invention. Fungus inoculation was accomplished by tapping leaves of previously infected barley and cucumber plants over the treated and untreated pots containing the barley and cucumber plants, respectively, to distribute spores of the fungus over the plants growing in the pots.

Six days after inoculation, disease control was evaluated on a 0 to 6 rating scale. A 0 rating was assigned when no disease was evidenced. A 6 rating was given for severe disease. Intermediate ratings were assigned depending on the degree of disease. Percent control was computed by comparing the ratings of the treated and untreated plants.

The results of this test are reported in Table 7 wherein systemic control of powdery mildew disease in barley is reported under the title "BMS 250." Control of cucumber powdery mildew disease is reported, in Table 7, under the title "CMS 250."

EXAMPLE 13

Control of Powdery Mildew Fungus by Foliar Application

Eight plants of barley (Variety "Herta") were planted in a pot. The number of pots, as in Example 12, were sufficient to accommodate testing in duplicate or triplicate for each of the 66 compounds tabulated in Tables 3 and 4. A number of pots, each containing eight barley plants, were left untreated as controls.

In this test each of the compounds formulated into emulsion compositions, at a concentration of 1,000 milligrams of the compound per liter of water (1,000 mg/l), were prepared. These emulsions were then sprayed onto the foliage of the barley plants. The pots in which the plants were unsprayed acted as controls.

After the foliage of the sprayed pots were dried the pots containing the sprayed and the unsprayed plants were all placed in a greenhouse maintained at 21° C. All the plants in the pots were thereupon inoculated with barley powdery mildew fungus, *Erysiphe graminis*. Inoculation of the fungus was again accomplished by distributing spores of the fungus over the leaves of the plants to be tested from plants which had previously been infected with the disease.

Five days after inoculation, the plants were evaluated and assigned a disease rating of 0 to 6 in accordance with the criterion explained in Example 12. Percentage control was computed in accordance with the description of Example 12. The results of these tests are summarized in Table 7 under the title "BMP 1,000."

Similarly, pinto bean plants were prepared, treated and inoculated with Erysiphe polygoni (PMP) as described above and reported in Table 7.

EXAMPLE 14

Control of Rice Blast Disease by Foliar Treatment

Five to ten rice plants (Variety "Bellemont") were grown in a plurality of pots. The number of pots utilized equalled two times the number of compounds of the present invention in Table I plus untreated control pots. The fungicide candidate pots were sprayed with emulsion compositions, formed in accordance with the procedure of Example 11, wherein each compound was provided in a concentration of 1,000 mg/l. This spraying occurred 3 to 4 weeks after planting of the plants in the pots. The controls remained unsprayed.

The sprayed and unsprayed plants, five to a pot, were inoculated with spores of the rice blast fungus, *Pyricularia oryzae*. This inoculation was accomplished by preparing inoculum containing 20,000 to 30,000 spores per milliliter. The inoculum was sprayed onto the plants to which one or two drops of ethoxylated sorbitan monolaurate surfactant had been earlier applied to ensure proper wetting of the inoculum onto the plant foliage.

The inoculated plants in the control and fungicide candidate pots were incubated in a control chamber, at a humidity of 99% and a temperature of 21° C., for about 24–48 hours to allow infection to occur. The plants, after 24–48 hours in the control chamber, were transferred to a greenhouse for six days to permit disease development to occur. Disease was manifested by blast lesions on the leaves. Disease control was calculated by one of two methods. In one method the number of lesions were counted, if infection was moderate. Alternatively, in the case of severe infection, disease was evaluated by the 0 to 6 rating system discussed in Example 12. Whichever disease control rating system was employed to determine disease control of any particular compound was also utilized in evaluating its control.

The results of this test are tabulated in Table 7 under the title of "RCB 1,000."

EXAMPLE 15

Control of Bean Rust Fungus Eradicant Test

Two pinto bean plants, *P. vulgaris*, were planted in a plurality of pots. When the plants were seven days old, at the primary leaf stage of growth, they were all sprayed with a suspension containing 20,000 spores of the bean rust fungus, *Uromyces phaseoli*, per milliliter of suspending water. All the pots containing the inoculated plants were then incubated in a controlled environmental chamber; maintained at 99% humidity and 21 ° C., for 24 hours to allow infection to develop. The plants were then removed from the incubator and allowed to dry. Two days after inoculation the infected plants were sprayed with compositions of the compounds tabulated in Tables 3 and 4. The compositions were prepared in accordance with the procedure of Example 11 to provide a dosage of 1,000 mg/l. A number of infected plants were not sprayed so that they could act as untreated controls. All the sprayed and unsprayed plants were placed in a greenhouse, maintained at a temperature of 21° C., for five days to allow any disease present to be expressed.

The sprayed and control plants were assessed for disease using the 0 to 6 rating system described in Example 12. Disease control, as discussed in Example 12, was then determined. The control of disease, expressed as percent reduction of disease, is included in Table 7 under the title "BRE 1,000."

EXAMPLE 16

Control of Peanut Cercospora Leafspot by Foliar Treatment

Eight Virginia peanut plants were grown in each of a plurality of pots. Enough pots were prepared so that each of the compounds listed in Tables 3 and 4, prepared as emulsion compositions in accordance with the procedure of Example 11, could be evaluated by spraying each of them on the sixteen plants (two pots having eight plants each). An equal number of pots, which were not sprayed, were provided as controls. Spraying occurred when the plants were four weeks old. The concentration of the emulsion utilized to spray the peanut plants was 900 mg/l.

All the plants, both sprayed and unsprayed (the controls), were thereafter inoculated with spores of Peanut Cercospora leafspot, *Cercospora arachidicola* or *Cercosporidium personatum*. The inoculum contained 20,000 to 30,000 spores per milliliter. The inoculum (which had been previously treated with one or two drops of ethoxylated sorbitan monolaurate to aid in wetting the leaves) was sprayed onto the leaves of the peanut plants. All the pots containing the inoculated peanut plants were incubated in a control chamber, maintained at 24° C., for 36 hours to develop infection. The plants were then placed in a greenhouse for 21 days to allow disease development.

After 21 days in the greenhouse, all the plants were taken out and evaluated using the 0 to 6 disease rating system. Percent control was computed and the results are reported in Table 7 under the title "PNT 900." In this column, those cases using Cercosporidium for Cercospora are indicated with footnote 1.

EXAMPLE 17

Control of Barley Blast by Foliar Treatment

A plurality of pots which included 10 plants of 6 day old barley (Variety "Herta") were prepared. These pots were sprayed with emulsion compositions, formulated in accordance with the procedure of Example 11, of each of the compounds set forth in Tables 3 and 4.

Each composition was sprayed on duplicate pots and a number of barley pots were left untreated as controls. All plants were inoculated with spores of the blast fungus, *Pyricularia oryzae*. The method of inoculation utilized was the same as that enumerated in Example 14, which employed the same fungus.

All the inoculated plants were placed in a greenhouse, maintained at a temperature of 21° C. and a humidity of 99%, for five days. At that time, the plants were evaluated using the 0 to 6 disease rating system. Percent control was computed and the results of this test are included in Table II under the title "BBL 1,000."

EXAMPLE 18

Control of Eight Fungus Species

Each of the compounds, Compound Nos. 1 to 66, listed in Tables 3 and 4 were solubilized in acetone at a concentration of 500 mg/l. Filter paper discs, each 11 mm. in diameter, were dipped in each of the test solutions. The discs were allowed to dry in air to drive off the acetone solvent. An equal number of discs were untreated and acted as controls.

Each of the treated and untreated discs were then placed on agar plates and seven fungus species: *Alternaria solani* (ALT), *Botrytis cinerea* (BOT), *Fusarium oxysporum* (FUS), *Helminthosporium maydis* (HMAY), *Phytophthora infestans* (PHY), *Sclerotinia sclerotiorum* (SCM) and *Sclerotium rolfsii* (SCO) were added to the center of each disc in the form of a culture plug with the fungus mat in contact with the treated paper of the test disc or, in the case of the controls, in contact with the untreated test paper. The plates were incubated at 29° C. in an oven.

In certain cases, which are marked in Table 7 with footnotes, the following organisms substitutions were made:

*Collectotrichum gossypii* for HMAY;
*Pythium ultimum* for PHY;
*Rhizoctonia solani* for SCM; and
*Septoria nodorum* for ALT Percent growth inhibition by the compounds of the present invention of the seven fungus species was evaluated, after incubation, by measuring the radius from the center of the fungus colony of the treated discs compared to the radius from the center of the fungus colony of the untreated discs. That is, inhibition effectuated by each of the compounds was determined as a function of the percent difference between the radii of the treated and untreated discs. The results of these tests appear in Table 7 under the titles "ALT 500," "BOT 500," "FUS 500," "HMAY 500," "PHY 500," "SCM 500," and "SCO 500", except where the substitute organisms were used and footnoted.

It is noted that in the case of the test of the fungus *Helminthosporium maydis*, the concentration of each of Compound Nos. 1 to 66 was 500 milligrams per liter.

A separate test was utilized to determine the control of a eighth fungi species, *Cercospora arachidicola* (CER). In this test two drops of the fungus were added as a spore suspension (20,000 spores per milliliter) to the chemically treated discs, rather than as a mycelial culture plug. Scoring of the effectiveness of the compounds in controlling the *Cercospora arachidicola* fungus was determined with control based on the following scoring criteria: 100 represented complete inhibition of germination and growth of the fungus; 80 represented nearly complete inhibition but some growth of the fungus; 50 represented partial inhibition of growth or early complete inhibition with later growth; 20 indicated some, but not significant, inhibition of growth; and 0 indicated complete growth of the fungus without any inhibition.

In certain cases indicated by a footnote in Table 7, *Cercosporidium personatum* was substituted for CER;

As in the case of the seven fungus species discussed above, the results representing the effectiveness of the compounds of Tables 3 and 4 against *Cercospora arachidicola* are included in Table 7 under the title "CER 500."

Table 7, containing the percent fungicidal control of Examples 11–18 for compounds 1–66, follows.

TABLE 7

| CMPD. NO. | ALT 500 EX. 18 | BBL 1000 EX. 17 | BMP 1000 EX. 13 | HMS 250 EX. 12 | BOT 500 EX. 18 | BRE 1000 EX. 15 | CER 500 EX. 18 | CMS 250 EX. 12 |
|---|---|---|---|---|---|---|---|---|
| 1 | 0 | 40 | 85 | 15 | 30 | 100 | 85 | 65 |
| 2 | 95 | 100 | 100 | 65 | 100 | 100 | 85 | 100 |
| 3 | 65 | 90 | 65 | 15 | 0 | 0 | 100 | 0 |
| 4 | 40 | 100 | 85 | 0 | 100 | 0 | 0 | 0 |
| 5 | 25 | 35 | 90 | 20 | 0 | 85 | 80 | 0 |
| 6 | 65 | 100 | 100 | 100 | 100 | 100 | 100 | 0 |
| 7 | 100 | 90 | 35 | 20 | 100 | 0 | 100 | 20 |
| 8 | 60 | 0 | 0 | 20 | 80 | 0 | 100 | 60 |
| 9 | 100 | 50 | 90 | 0 | 90 | 0 | 100 | 40 |
| 10 | 100 | 90 | 100 | 20 | 100 | 0 | 100 | 80 |
| 11 | 85 | 90 | 90 | 80 | 100 | 0 | 100 | 80 |
| 12 | 70 | 0 | 100 | 20 | 85 | 0 | 100 | 20 |
| 13 | 50 | 0 | 0 | 20 | 80 | 0 | 100 | 60 |
| 14 | 50 | 0 | 15 | 0 | 80 | 0 | 100 | 0 |
| 15 | 70 | 90 | 100 | 0 | 100 | 100 | 100 | 0 |
| 16 | 87 | 90 | 100 | 0 | 50 | 100 | 100 | 0 |

TABLE 7-continued

| | | | | | | | | |
|---|---|---|---|---|---|---|---|---|
| 17 | 35 | 0 | 0 | 0 | 50 | 100 | 100 | 0 |
| 18 | 80 | 50 | 85 | 0 | 10 | 100 | 100 | 0 |
| 19 | 90 | 0 | 0 | 0 | 100 | 100 | 100 | 0 |
| 20 | 40 | 85 | 90 | 0 | 98 | 95 | 100 | 0 |
| 21 | 0 | 90 | 90 | 0 | 25 | 95 | 100 | 0 |
| 22 | 60 | 15 | 100 | 80 | 100 | 100 | 100 | 90 |
| 23 | 100 | 100 | 100 | 50 | 40 | 100 | 0 | 0 |
| 24 | 100 | 85 | 100 | 85 | 50 | 100 | 0 | 0 |
| 25 | 100 | 0 | 0 | 15 | 60 | 100 | 0 | 100 |
| 26 | 90 | 85 | 100 | 100 | 30 | 100 | 100 | 50 |
| 27 | 25 | 0 | 0 | 0 | 60 | 60 | 100[1] | 100 |
| 28 | 35 | 75 | 100 | 85 | 20 | 95 | 0 | 80 |
| 29 | 45 | 10 | 20 | 40 | 40 | 90 | 100 | 0 |
| 30 | 25 | 100 | 100 | 0 | 35 | 0 | 0 | 0 |
| 31 | 25 | 90 | 100 | 0 | 50 | 65 | 0 | 0 |
| 32 | 30 | 100 | 100 | 0 | 50 | 65 | 0 | 0 |
| 33 | 25 | 100 | 100 | 0 | 80 | 100[1] | 0[1] | 0 |
| 34 | 30[5] | 100 | 100 | 0 | 30 | 0 | 0[1] | 0 |
| 35 | 50 | 90 | 75 | 0 | 50 | 50 | 100 | 25 |
| 36 | 100 | 90 | 100 | 100 | 100 | 100 | 100 | 90 |
| 37 | 100 | — | — | 80 | 100 | 100 | 100 | 0 |
| 38 | 100 | 90 | 100 | 93 | 100 | 100 | 100 | 0 |
| 39 | 100 | — | — | 0 | 100 | 100 | 100 | 80 |
| 40 | 100 | — | — | 90 | 100 | 100 | 100 | 60 |

| CMPD. NO. | FUS 500 EX.18 | HMAY 500 EX.18 | PHY 500 EX.18 | PMP 1000 EX. 18 | PNT 900 EX. 16 | RCB 1000 EX. 14 | SCM 500 EX. 18 | SCO 500 EX. 18 |
|---|---|---|---|---|---|---|---|---|
| 1 | 60 | 65 | 0 | 0 | — | 0 | 0 | 0 |
| 2 | 100 | 0 | 95 | 60 | 65 | 65 | 0 | 0 |
| 3 | 0 | 0 | 50 | 0 | — | — | 25 | 25 |
| 4 | 50 | 15 | 40 | 25 | — | — | 0 | 0 |
| 5 | 35 | 30 | 85 | 15 | 10 | — | 0 | 0 |
| 6 | 100 | 100 | 100 | 100 | — | — | 0 | 30 |
| 7 | 100 | 85 | 100 | 0 | 20 | | 55 | 100 |
| 8 | 60 | 654 | 85 | 0 | | | 0 | 60 |
| 9 | 100 | 95 | 100 | 0 | 70 | — | 35 | 100 |
| 10 | 100 | 100 | 100 | 0 | 60 | — | 55 | 85 |
| 11 | 100 | 75 | 100 | 0 | 50 | | 55 | 50 |
| 12 | 65 | 95 | 100 | 0 | 85 | | 75 | 100 |
| 13 | 50 | 55 | 70 | 0 | 42 | | 0 | 40 |
| 14 | 55 | 45 | 50 | 0 | 70 | | 0 | 60 |
| 15 | 100 | 100 | 100 | 90 | 92 | 25 | 45 | 45 |
| 16 | 100 | 100 | 100 | 50 | 33 | 33 | 15 | 55 |
| 17 | 90 | 75 | 94 | 0 | 83 | — | 5 | 40 |
| 18 | 100 | 90 | 80 | 25 | 67 | — | 5 | 15 |
| 19 | 100 | 100 | 100 | 65 | — | — | 5 | 15 |
| 20 | 60 | 35 | 25 | 50 | 33 | — | 0 | 0 |
| 21 | 60 | 80 | 0 | 95 | 75 | 83 | 0 | 0 |
| 22 | 0 | 75 | 40 | 90 | — | — | 0 | 50 |
| 23 | 45 | 100 | 70 | 95 | — | — | 55 | — |
| 24 | 55 | 75 | 50 | 95 | — | — | 55 | — |
| 25 | 90 | 95 | 95 | 60 | — | — | 20 | — |
| 26 | 85 | 75 | 60 | 70 | 20 | — | 50 | — |
| 27 | 100 | 40[2] | 10[3] | 40 | — | — | 15[4] | 0 |
| 28 | 15 | 55 | 0 | 0 | — | — | 35 | 20 |
| 29 | 20 | 75 | 5 | 90 | 0 | — | 35 | 84 |
| 30 | 20 | 35 | 40 | 0 | — | — | 40 | 40 |
| 31 | 50 | 60 | 0 | 90 | — | 20 | 30 | |
| 32 | | 50 | 60 | 0 | 90 | — | 20 | 30 |
| 33 | 30 | 35[2] | 45[3] | 0 | — | — | 0[4] | 40 |
| 34 | 30 | 35[2] | 45[3] | 0 | — | — | 0[4] | 40 |
| 35 | 65 | 35 | 100 | 20 | 0 | — | 0 | 0 |
| 36 | 100 | 100 | 100 | 20 | 96 | 50 | 5 | 100 |
| 37 | 100 | 100 | 100 | 100 | 96 | 42 | 0 | 90 |
| 38 | 100 | 100 | 100 | 25 | 100 | 58 | 5 | 100 |
| 39 | 100 | 100 | 100 | 90 | 88 | — | 25 | 100 |
| 40 | 100 | 100 | 100 | 90 | 75 | 0 | 25 | 0 |

| CMPD. NO. | ALT 500 EX. 18 | BBL 1000 EX. 17 | BMP 1000 EX. 13 | HMS 250 EX. 12 | BOT 500 EX. 18 | BRE 1000 EX. 15 | CER 500 EX. 18 | CMS 250 EX. 12 |
|---|---|---|---|---|---|---|---|---|
| 41 | 100 | 100 | 100 | 55 | 75 | 100 | 100 | 20 |
| 42 | 100 | 100 | 100 | 10 | 100 | 100 | 100 | 10 |
| 43 | 100 | 100 | 100 | 80 | 100 | 100 | 100 | 45 |
| 44 | 100 | 90 | 100 | 100 | 90 | 100 | 100 | 65 |
| 45 | 100 | 50 | 100 | 100 | 75 | 100 | 100 | 0 |

TABLE 7-continued

| | | | | | | | | |
|---|---|---|---|---|---|---|---|---|
| 46 | 100 | 35 | 20 | 100 | 65 | 100 | 100 | 0 |
| 47 | 25 | 85 | 100 | 0 | 80 | 100 | 100 | 0 |
| 48 | 90 | 0 | 80 | 65 | 90 | 100 | 100 | 60 |
| 49 | 95 | 65 | 65 | 0 | 75 | 100 | 100[1] | 0 |
| 50 | 20 | 0 | 0 | 0 | 65 | 40 | 0[1] | 100 |
| 51 | 100 | 100 | 100 | 0 | 95 | 100 | 80[1] | 85 |
| 52 | 80[5] | 0 | 85 | 50 | so | 0 | 100[1] | 0 |
| 53 | 100 | — | — | 85 | 60 | 100 | 100[1] | 100 |
| 54 | 20 | 100 | 100 | 0 | 15 | 0 | 100 | 0 |
| 55 | 35 | 100 | 100 | 0 | 18 | 0 | 100 | 0 |
| 56 | 60 | 0 | 0 | 40 | 5 | 95 | 100 | 0 |
| 57 | 80 | 10 | 0 | 20 | 70 | 100 | 100 | 0 |
| 58 | 55 | 15 | 100 | 100 | 100 | 100 | 100 | 100 |
| 59 | 65 | — | — | 0 | 80 | 75 | 100 | 0 |
| 60 | 55 | 100 | 100 | 0 | 35 | 95 | 100[1] | 0 |
| 61 | 80 | 65 | 0 | 0 | 20 | 0 | 100[1] | 0 |
| 62 | 5 | 85 | 100 | 0 | 70 | 0 | 25 | 45 |
| 63 | 60 | — | — | 0 | 55 | 100 | 0 | 0 |
| 64 | 35 | 100 | 100 | 0 | 10 | 90 | 0 | 0 |
| 65 | 55 | 100 | 100 | 0 | 50 | 0 | 100[1] | 0 |
| 66 | 80[5] | 0 | 0 | 0 | 40 | 0 | 0[1] | 0 |

| CMPD. NO. | FUS 500 EX. 18 | HMAY 500 EX. 18 | PHY 500 EX. 18 | PMP 1000 EX. 18 | PNT 900 EX. 16 | RCB 1000 EX. 14 | SCM 500 EX. 18 | SCO 500 EX. 18 |
|---|---|---|---|---|---|---|---|---|
| 41 | 100 | 100 | 90 | 90 | 75 | — | 0 | 0 |
| 42 | 100 | 100 | 100 | 100 | 88 | — | 35 | 100 |
| 43 | 100 | 100 | 100 | 100 | 83 | — | 25 | 100 |
| 44 | 100 | 100 | 100 | 100 | 25 | — | 60 | 20 |
| 45 | 100 | 100 | 100 | 75 | 20 | 20 | 25 | — |
| 46 | 100 | 100 | 100 | 95 | — | — | 35 | — |
| 47 | 100 | 100 | 90 | 80 | 0 | — | 30 | — |
| 48 | 100 | 100 | 90 | 40 | 50 | — | 21 | — |
| 49 | 100 | 100[2] | 100[3] | 85 | — | — | 45[4] | 25 |
| 50 | 85 | 70[2] | 25[3] | 30 | — | — | 20[4] | 5 |
| 51 | 85 | 100[2] | 65[3] | 100 | — | 75 | 40[4] | 100 |
| 52 | 85 | 80[2] | 85[3] | 0 | — | — | 50[4] | 50 |
| 53 | 100 | 100[2] | 45[3] | 95 | — | — | 50[4] | 90 |
| 54 | 20 | 40 | 10 | 0 | — | — | 85 | 0 |
| 55 | 55 | 30 | 10 | 0 | — | — | 35 | 0 |
| 56 | 40 | 45 | 5 | 95 | — | — | 10 | — |
| 57 | 90 | 90 | 95 | 100 | 0 | — | 25 | 76 |
| 58 | 85 | 100 | 100 | 95 | 50 | — | 20 | 10 |
| 59 | 80 | 70 | 85 | 95 | — | — | 5 | 35 |
| 60 | 55 | 65 | 45 | 0 | — | — | 30 | 0 |
| 61 | 85 | 60[2] | 35[3] | 0 | — | — | 40[4] | 5 |
| 62 | 0 | 90 | 0 | 90 | — | — | 20 | 30 |
| 63 | 100 | 70 | 15 | 100 | — | — | 25 | 10 |
| 64 | 25 | 15 | 40 | 75 | — | — | 30 | 20 |
| 65 | 45 | 65 | 50 | 0 | — | — | 35 | 0 |
| 66 | 70 | 50[2] | 50[3] | 0 | — | — | 0[4] | 45 |

KEY TO NOTES:
SUBSTITUTION OF FUNGUS SPECIES
1. COSP FOR CER
2. COLL FOR HMAY
3. PYTH FOR PHY
4. RHIZOC FOR SCM
5. SEPT FOR ALT

The above embodiments and examples are given to illustrate the scope and spirit of the instant invention. These embodiments will make apparent, to those skilled in the art, other embodiments and examples. These other embodiments and examples are within the contemplation of the present invention. Therefore, this invention should be limited only by the appended claims.

What is claimed is:

1. A compound having the structural formula

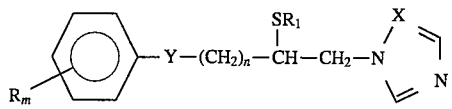

wherein:

R can be the same or different and is halogen, hydrogen, $C_1$–$C_8$ alkyl, $C_1$–$C_8$ haloalkyl, $C_3$–$C_6$ cycloalkyl, $C_7$–$C_9$ aralkyl, phenyl, nitro, $C_1$–$C_6$ alkoxy, $C_1$–$C_6$ alkylthio, $C_1$–$C_6$ alkylsulfinyl, $C_1$–$C_6$ alkylsulfonyl, $C_7$–$C_9$ aralkoxy, phenoxy, phenylthio, phenylsulfinyl, or phenylsulfonyl;

m is an integer from 0 to 5;

Y is $CH_2$ n is an integer from 1 to 5;

$R_1$ is $C_1$–$C_5$ alkyl;

X is N; or physiologically acceptable salts thereof.

2. A compound in accordance with claim 1 wherein R is halogen or $C_2$–$C_4$ alkyl; m is 1 or 2; and $R_1$ is $C_2$–$C_4$ alkyl; or physiologically acceptable salts thereof.

3. A fungicidal composition comprising A) a fungicidally effective amount of a compound of claim 1, and B) a suitable carrier therefor.

4. A method for controlling phytopathogenic fungi comprising applying a fungicidally effective amount of the compound of claim 1 to a locus to be protected.

5. A method in accordance with claim 4 wherein the compound is applied to plant foliage in a concentration in the range of between about 10 and about 500 milligrams per liter.

6. A method in accordance with claim 4 wherein the compound is applied to soil in a concentration in the range of between about 0.125 and about 10 kilograms per hectare.

7. A method in accordance with claim 4 wherein the compound is applied as a seed coating in a concentration in the range of between about 5 and about 75 grams of compound per 100 kilograms of seed.

* * * * *